United States Patent
Conrad et al.

(10) Patent No.: US 11,207,309 B2
(45) Date of Patent: Dec. 28, 2021

(54) READY-TO-ADMINISTER FENTANYL FORMULATIONS

(71) Applicant: Hikma Pharmaceuticals International Limited, London (GB)

(72) Inventors: Andrew Conrad, Bedford, OH (US); Ragheb Al-Shakhshir, Bedford, OH (US); Ragheb AbuRmaileh, Bedford, OH (US)

(73) Assignee: Hikma Pharmaceuticals International Limited, London (GB)

( * ) Notice: Subject to any disclaimer, the term of this patent is extended or adjusted under 35 U.S.C. 154(b) by 0 days.

(21) Appl. No.: 16/670,031

(22) Filed: Oct. 31, 2019

(65) Prior Publication Data

US 2021/0015808 A1   Jan. 21, 2021

Related U.S. Application Data

(60) Provisional application No. 62/876,067, filed on Jul. 19, 2019.

(51) Int. Cl.
*A61K 31/4468* (2006.01)
*A61K 9/00* (2006.01)

(52) U.S. Cl.
CPC ........ *A61K 31/4468* (2013.01); *A61K 9/0019* (2013.01)

(58) Field of Classification Search
CPC ................................................ A61K 31/4468
USPC ....................................................... 514/329
See application file for complete search history.

(56) References Cited

U.S. PATENT DOCUMENTS

| 4,486,423 A | 12/1984 | Kenyhercz |
| 6,139,866 A | 10/2000 | Chono et al. |
| 10,206,872 B2 | 2/2019 | Kumar et al. |
| 2003/0138508 A1 | 7/2003 | Novak et al. |
| 2015/0283123 A1 | 10/2015 | Watts et al. |
| 2019/0117560 A1 | 4/2019 | Kumar et al. |

FOREIGN PATENT DOCUMENTS

WO   2020021567 A1   1/2020

OTHER PUBLICATIONS

McKluskey et al., Am. J. Health Syst. Pharm (2009) vol. 66(9), pp. 860-863 (abstract).*
Anderson et al., Pharmacy Base (2015) vol. 3(4), pp. 379-385.*
The International Search Report and Written Opinion issued in corresponding International PCT Application No. PCT/IB2019/001182; dated Apr. 7, 2020.
Highlights of Prescribing Information for Fentanyl Citrate Injection, 2017 (label).

* cited by examiner

*Primary Examiner* — Taofiq A Solola
(74) *Attorney, Agent, or Firm* — Pearne & Gordon LLP

(57) ABSTRACT

The stable liquid formulations for parenteral administration include fentanyl or a pharmaceutically acceptable salt thereof. The formulations include a diluent and buffer, either containing sodium, in an aqueous solution that has a pH of about 3 to about 4.5. The parenteral liquid formulations are stable formulations that are supplied as a ready-to-administer product in an infusion container or bag. The stable formulations are terminally sterilized in the infusion container. The stable formulations are suitable for administration to a patient in need of therapy with fentanyl or a pharmaceutically acceptable salt thereof.

9 Claims, No Drawings

READY-TO-ADMINISTER FENTANYL FORMULATIONS

FIELD

The invention relates to stable liquid formulations containing fentanyl or a pharmaceutically acceptable salt thereof as an active ingredient and, in particular, ready-to-administer parenteral liquid formulations containing fentanyl citrate, diluent and a buffer that are stable.

BACKGROUND

Fentanyl, chemically known as N-phenyl-N-[1-(2-phenylethyl)piperidin-4-yl]propanamide, is used as an opioid receptor agonist in patients to provide pain relief or analgesic action, for instance, those undergoing open heart surgery or certain complicated neurological or orthopedic procedures. Fentanyl is typically used in the citrate salt form. Fentanyl citrate is conventionally available in an injectable form as a solution in glass ampules or vials containing 50 mcg fentanyl base per milliliter (mL) and volumes of 1 mL, 2 mL, 5 mL, 20 mL and 50 mL. The injection product is a preservative-free solution that includes fentanyl citrate, water for injection, sodium hydroxide and/or hydrochloric acid, if needed, for pH adjustment in the range of 4.0 to 7.5.

The stability of commercially available solutions, once diluted, is limited and not intended for long term storage. Thus, the diluted solutions are administered shortly after being formed and storage of the diluted solutions results in unacceptable loss of fentanyl concentration. Fentanyl has a tendency to absorb onto plastic components like those of an infusion bag, particularly during terminal sterilization, which results in loss of concentration of the active ingredient. Thus, known formulations of fentanyl citrate cannot be terminally sterilized in an IV bag due to assay loss. Dilution of vial solutions also suffers from the disadvantage of time-consuming dilution steps that introduce potential undesirable impurities with the use of external components. Dilution also can introduce the potential for error in mixing and measuring such components, and increases the risk for contamination and lack of sterility.

There remains a need for ready-to-administer injectable formulations of fentanyl that offer long-term storage stability and be terminally sterilized after filling such as in an infusion container under standard overkill cycle conditions with reduced loss of fentanyl concentration. The present invention provides stable liquid formulations for parenteral administration of fentanyl that minimize the number of ingredients and exhibit enhanced storage stability in a ready-to-administer presentation.

SUMMARY

Described herein are stable parenteral liquid formulations of fentanyl or salts thereof that include a non-sugar, non-saccharide, or non-sugar alcohol diluent, a buffer, and optionally along with a pH adjuster (e.g., sodium hydroxide, hydrochloric acid). The formulations have an acidic pH in the range of about 3 to about 4.5, and preferably about 3.8 to about 4.2. The formulations, for instance as described in the aspects below, can be terminally sterilized or aseptically filled in an infusion container. The formulations exhibit improved stability at standard and accelerated storage conditions, for example, such that no individual degradation product or impurity is present at more than 1 weight percent based on the total weight of the formulation after storage at about 40° C. for 3 months or more, or 6 months or more. In another example, the formulations are stable for 3 months, 6 months or more, or 12 months or more at about 25° (long-term stability storage) and about 40° C. (accelerated stability storage) characterized by about 95% or more, or about 98% or more, of the initial concentration of fentanyl (e.g., fentanyl citrate) remaining present in the formulation as compared to the initial concentration prior to terminal sterilization in an infusion container. In yet another example, the formulations are stable for 3 months or more, 6 months or more, or 12 months or more at about 25° and about 40° C. characterized by a total impurity content of about 1 weight percent or less, or 0.5 weight percent or less based on the total weight of the formulation.

In a first aspect, there is disclosed a ready-to-administer parenteral liquid formulation that includes fentanyl or a pharmaceutically acceptable salt thereof, a non-sugar or non-saccharide or non-sugar alcohol diluent, a buffer, and the formulation has a pH of about 3 to about 4.5 and is terminally sterilized in an infusion container and stable for at least 6 months or at least 12 months at about 40° C. For example, the formulation is free of a sugar-based or saccharide-containing diluent.

In an example of aspect 1, the fentanyl or a pharmaceutically acceptable salt thereof is fentanyl citrate.

In another example of aspect 1, the fentanyl or a pharmaceutically acceptable salt thereof is present at a concentration of from about 5 mcg/mL to about 25 mcg/mL based on the total volume of the formulation.

In another example of aspect 1, the fentanyl is present at a concentration selected from about 5 mcg/mL, about 10 mcg/mL and about 20 mcg/mL based on the total volume of the formulation.

In another example of aspect 1, the formulation is stored in an infusion container and terminally sterilized, for example, by autoclaving.

In another example of aspect 1, the formulation has a total volume of from about 50 mL to about 500 mL and is stored in an infusion container.

In another example of aspect 1, the formulation is stored in an infusion bag made from flexible polymeric material.

In another example of aspect 1, the pH of the formulation is about 3.5 to about 4.5 or about 3.8 to about 4.2. In another example, the pH is about 3 to about 3.5 or less.

In another example of aspect 1, the diluent contains sodium, for example, the diluent is aqueous sodium chloride solution.

In another example of aspect 1, the formulation is preservative free.

In another example of aspect 1, the formulation is free of a chelating agent.

In another example of aspect 1, the buffer includes at least one of acetate, glutamate, citrate, tartrate, benzoate, lactate, malate, gluconate, phosphate and glycine.

In another example of aspect 1, the buffer is citric acid, sodium citrate or a combination thereof.

In another example of aspect 1, the buffer includes acetic acid, sodium acetate or a combination thereof.

In another example of aspect 1, the buffer is present in the formulation at a concentration of from about 0.5 mg/mL to about 5 mg/mL.

In another example of aspect 1, the formulation further includes a pH adjuster.

In another example of aspect 1, the formulation contains about 1.0% or less of an individual impurity after storage for 6 months or 12 months at about 40° C. or for 12 months at about 25° C. The pH of the formulation can be in the range of about 3.5 to about 4.5, about 3.8 to about 4.2 or about 3 to about 3.5.

In another example of aspect 1, the formulation contains about 1.0% or less of total impurities after storage for 6 months or 12 months at about 40 2° C. or for 12 months at about 25° C. The pH of the formulation can be in the range of about 3.5 to about 4.5, about 3.8 to about 4.2 or about 3 to about 3.5.

In another example of aspect 1, the formulation retains about 95% or more of the initial concentration of fentanyl or a pharmaceutically acceptable salt thereof after storage for 6 months or 12 months at about 40° C. or for 12 months at about 25° C. The pH of the formulation can be in the range of about 3.5 to about 4.5, about 3.8 to about 4.2 or about 3 to about 3.5.

In another example of aspect 1, the formulation retains about 98% or more of the initial concentration of fentanyl or a pharmaceutically acceptable salt thereof after storage for 6 months or 12 months at about 40 or for 12 months at about 25° C. The pH of the formulation can be in the range of about 3.5 to about 4.5, about 3.8 to about 4.2 or about 3 to about 3.5.

In a second aspect, there is disclosed a ready-to-administer parenteral liquid formulation that includes 5 mcg/mL to about 25 mcg/mL of fentanyl citrate, a sodium-containing diluent, and about 0.5 mg/mL to about 5 mg/mL of a buffer, wherein the ready-to-administer parenteral liquid formulation has a pH of about 3 to about 4.5 and has been terminally sterilized in a polymeric infusion container, and the formulation is stable for at least 6 months or at least 12 months at about 25° C. or about 40° C.

In an example of aspect 2, the buffer includes citric acid, sodium citrate or a combination thereof.

In another example of aspect 2, the buffer includes acetic acid, sodium acetate or a combination thereof.

In another example of aspect 2, the polymeric infusion container is terminally sterilized by autoclaving.

In another example of aspect 2, the polymeric infusion container is a bag and the formulation has a volume of from about 50 mL to about 500 mL.

In another example of aspect 2, the formulation is free of a chelating agent.

In another example of aspect 2, the sodium-containing diluent is a non-sugar or non-sugar alcohol diluent.

In another example of aspect 2, the formulation is free of a sugar or sugar-alcohol.

In another example of aspect 2, the sodium-containing diluent is aqueous sodium chloride solution.

In another example of aspect 2, the pH of the formulation is in the range of about 3.5 to about 4.5, about 3.8 to about 4.2 or about 3 to about 3.5.

In another example of aspect 2, the formulation contains about 1.0% or less of an individual impurity after storage for 6 months or 12 months at about 40° C. or for 12 months at about 25° C. The pH of the formulation can be in the range of about 3.5 to about 4.5, about 3.8 to about 4.2 or about 3 to about 3.5.

In another example of aspect 2, the formulation contains about 1.0% or less of total impurities after storage for 6 months or 12 months at about 40° C. or for 12 months at about 25° C. The pH of the formulation can be in the range of about 3.5 to about 4.5, about 3.8 to about 4.2 or about 3 to about 3.5.

In another example of aspect 2, the formulation retains about 98% or more of the initial concentration of fentanyl or a pharmaceutically acceptable salt thereof after storage for 6 months or 12 months at about 40° C. or for 12 months at about 25° C. The pH of the formulation is in the range of about 3.5 to about 4.5, about 3.8 to about 4.2 or about 3 to about 3.5.

In a third aspect, there is disclosed a ready-to-administer parenteral liquid formulation that essentially includes 5 mcg/mL to about 25 mcg/mL of fentanyl citrate, a sodium-containing diluent, about 0.5 mg/mL to about 5 mg/mL of a buffer, one or more pH adjusters, and, optionally, a chelating agent, wherein the ready-to-administer parenteral liquid formulation has a pH of about 3 to about 4.5 and a volume of from about 50 mL to about 500 mL, wherein the formulation has been terminally sterilized in a polymeric infusion container, and after being terminally sterilized the formulation retains about 98% or more of the initial concentration of fentanyl or a pharmaceutically acceptable salt thereof after storage for 6 months or 12 months at about 40° C. or for 12 months at about 25° C.

In an example of aspect 3, the buffer includes citric acid, sodium citrate or a combination thereof, wherein the pH of the formulation is in the range of about 3.5 to about 4.5, about 3.8 to about 4.2 or about 3 to about 3.5.

In another example of aspect 3, the buffer includes acetic acid, sodium acetate or a combination thereof, wherein the pH of the formulation is in the range of about 3.5 to about 4.5, about 3.8 to about 4.2 or about 3 to about 3.5.

In another example of aspect 3, the formulation is free of a sugar or sugar-alcohol.

In another example of aspect 3, the pH of the formulation is in the range of about 3.5 to about 4.5, about 3.8 to about 4.2 or about 3 to about 3.5.

In another example of aspect 3, the formulation retains about 99% or more of the initial concentration of fentanyl or a pharmaceutically acceptable salt thereof after storage for 6 months or 12 months at about 40° C. or for 12 months at about 25° C. The pH of the formulation can be in the range of about 3.5 to about 4.5, about 3.8 to about 4.2 or about 3 to about 3.5.

In another example of aspect 3, the formulation contains about 1.0% or less of total impurities after storage for 6 months or 12 months at about 40° C. or for 12 months at about 25° C. The pH of the formulation can be in the range of about 3.5 to about 4.5, about 3.8 to about 4.2 or about 3 to about 3.5.

In a fourth aspect, there is disclosed a method of treating a patient in need of anesthesia by administering to the patient a ready-to-administer parenteral liquid formulation of aspects 1, 2 or 3.

In an example of aspect 4, the anesthesia is general or regional anesthesia.

In another example of aspect 4, the formulation is administered as an anesthetic premedication.

In a fifth aspect, there is disclosed the formulations of aspects 1 through 4 above, wherein the storage is either for long-term stability or accelerated stability for 3, 6 or 12 months. The storage temperature at long-term stability is about 25° C. or 25±2° C. and storage temperature at accelerated stability is about 40° C. or 40±2° C. for the specified storage time period. The storage conditions for stability measurements can further include a relative humidity. For example, long-term stability storage can be at about 25° C. at about 60% relative humidity or at 25±2° C. at 60±5% relative humidity (RH) at 3, 6 or 12 months. In another example, accelerated stability storage can be at about 40° C. at about 75% relative humidity or at 40±2° C. at 75±5% relative humidity (RH) at 3, 6 or 12 months.

In an example of aspect 5, the storage conditions for long-term stability of aspect 5, about 25° C. at about 60% relative humidity or at 25±2° C. at 60±5% relative humidity (RH), can apply to the formulations of aspects 1 through 4 for specifying that the formulations contain about 1.0% or less of an individual impurity after storage for 6 months or 12 months, contain about 1.0% or less of total impurities after storage for 6 months or 12 months, retain about 95% or more, about 98% or more, or about 99% or more of the initial concentration of fentanyl or a pharmaceutically acceptable salt thereof after storage for 6 months or 12 months, wherein the pH of the formulations can be in the range of about 3.5 to about 4.5, about 3.8 to about 4.2 or about 3 to about 3.5.

In an example of aspect 5, the storage conditions for accelerated stability of aspect 5, about 40° C. at about 75% relative humidity or at 40±2° C. at 75±5% relative humidity (RH), can apply to the formulations of aspects 1 through 4 for specifying that the formulations contain about 1.0% or less of an individual impurity after storage for 6 months or 12 months, contain about 1.0% or less of total impurities after storage for 6 months or 12 months, retain about 95% or more, about 98% or more, or about 99% or more of the initial concentration of fentanyl or a pharmaceutically acceptable salt thereof after storage for 6 months or 12 months, wherein the pH of the formulations can be in the range of about 3.5 to about 4.5, about 3.8 to about 4.2 or about 3 to about 3.5.

Any one of the above aspects (or examples of those aspects) may be provided alone or in combination with any one or more of the examples of that aspect discussed above; e.g., the first aspect may be provided alone or in combination with any one or more of the examples of the first aspect discussed above; and the second aspect may be provided alone or in combination with any one or more of the examples of the second aspect discussed above; and so-forth.

Additional features and advantages will be set forth in the detailed description which follows, and in part will be readily apparent to those skilled in the art from that description or recognized by practicing the embodiments as described herein, including the detailed description which follows, and the claims. It is to be understood that both the foregoing general description and the following detailed description are merely exemplary, and are intended to provide an overview or framework to understanding the nature and character of the claims.

DETAILED DESCRIPTION

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

Herein, when a range such as 5-25 (or 5 to 25) is given, this means preferably at least or more than 5 and, separately and independently, preferably not more or less than 25. In an example, such a range defines independently 5 or more, and separately and independently, 25 or less.

The present disclosure is directed to stable liquid formulations that include fentanyl or a pharmaceutically acceptable salt thereof and a sodium-containing diluent, a sodium-containing buffer or combination thereof. In one or more embodiments, the formulations are terminally sterilized and remain stable post sterilization. In one or more embodiments, the formulations include a non-sugar or non-sugar alcohol diluent, for example, an aqueous sodium-containing solution. The formulations can optionally include one or more pH adjusters, if necessary, e.g., in an aqueous solution, to adjust the pH of the formulations to be about 3 to about 4.5. The formulations can be terminally sterilized in an infusion container after filling and remain stable for at least 3, at least 6, or at least 12 months or more. In yet other embodiments, the formulations are stable and can be processed and filled aseptically under sterile environment conditions without terminal sterilization or autoclave.

The formulations of fentanyl are ideally ready-to-administer (RTA) formulations for parenteral administration without the need for reconstitution or further dilution. The ready-to-administer formulations are liquid stored in a pharmaceutically suitable container, for example, an infusion container such as polymeric container (e.g., intravenous bag). Diluents can include, for instance, fluids suitable for parenteral administration such as sodium chloride solutions.

The liquid parenteral formulations of the present disclosure are stable or exhibit stability when stored, such as after terminal sterilization, which includes formulation properties that may be affected by storage conditions, for example, active ingredient strength or concentration, impurities (e.g., individual components and total) and visual appearance characteristics (e.g., color, clarity, cloudy, haze, precipitates, etc.). Storage conditions that may affect stability can include, for example, storage temperature, humidity (e.g., relative), light exposure and storage time period.

In one or more embodiments, stability can include the amount of total impurities, inclusive of degradation products, that are formed after formation of the fentanyl formulations, for instance after terminal sterilization in an infusion container. The formation of impurities is measured for a specified period of time at specified storage conditions (e.g., temperature, humidity) minus the initial total impurities as measured following formation, for example, within the first 24 hours of formation (e.g., after terminal sterilization in an infusion container), which is the baseline or initial impurity measurement. In one or more embodiments, the formed fentanyl formulations of the present invention are stored in and terminally sterilized in a pharmaceutically acceptable infusion container within the first hour, about 2 hours, about 6 hours, about 12 hours or about 24 hours after formation. In other embodiments, the time period between filling the formed fentanyl formulations in a pharmaceutically acceptable infusion container and terminally sterilizing the container can be in the range of about 1 to about 7 days, or about 2 days, about 3 days, about 4 days, about 5 days or about 6 days.

In one or more embodiments, a liquid, ready-to-administer parenteral fentanyl formulation includes a formulation that retains about 95% or more, about 97% or more, about 97.5% or more, about 98% or more, about 98.5% or more, about 99% or more, or about 99.5% or more of the initial concentration of fentanyl or pharmaceutically acceptable salt thereof in the formulation after being terminally-sterilized in an infusion container and then stored under long-term (about 25° C.) or accelerated conditions (about 40° C.). As used herein, storage conditions for stability purposes can be either for long-term stability storage or accelerated stability storage, for instance, for 3, 6 or 12 months or more. The storage temperature at long-term stability is about 25° C. or 25±2° C. and storage temperature at accelerated stability is about 40° C. or 40±2° C. for the specified storage time period. The storage conditions for stability measurements can further include a relative humidity. For example, long-term stability storage can be at about 25° C. at about 60% relative humidity or at 25±2° C. at 60±5% relative humidity (RH) at a specified storage period, e.g., 3, 6 or 12 months. In another example, accelerated stability storage can be at about 40° C. at about 75% relative humidity or at 40±2° C. at 75±5% relative humidity (RH) at a specified storage period, e.g., 3, 6 or 12 months. Initial concentration of fentanyl or a pharmaceutically acceptable salt can be measured shortly after formation, filling (e.g., aseptic) and/or terminal sterilization of the formulation in a pharmaceutically acceptable container (e.g., polymeric infusion bag) prior to storage. For example, filling of the formulation in an infusion container can be within 24 hours of formation of the formulation. In one or more embodiments, a stable fentanyl formulation includes a formulation that contains about 0.25% or less, about 0.5% or less, about 0.75% or less, or about 1.0% or less of an individual impurity (e.g., a degradation impurity or fentanyl-related degradation impurity) formed after formation of the formulation and present after terminally sterilizing in an infusion container and storage under long term or accelerated conditions (i.e. about 25° C. and about 40° C.) for about 1, about 2, about 3, about 6, or about 12 or more months. Any measured individual impurity for purposes of measuring stability of a formulation herein does not include any impurity present in any ingredient prior to formation, filing and terminal sterilization of the fentanyl formulation. That is, as used herein, an impurity or impurities in an invented formulation refers to any impurity, including a degradation product, formed after formation, filing and terminal sterilization of the formulations.

In one or more embodiments, a stable ready-to-administer parenteral fentanyl formulation includes a formulation that contains about 0.25% or less, about 0.5% or less, about 1.0% or less, about 1.5% or less, or about 2.0% or less of total impurities or fentanyl-related degradation product present after storage under standard or accelerated conditions. Impurities and degradation products, whether individual or total, can be measured by conventional methods, for example, liquid chromatography (e.g., HPLC). In an example, a stable fentanyl formulation includes about 0.5% or less, about 0.4% or less, about 0.35% or less, or about 0.3% or less of total impurities after storage of the formulation at about 25° C. for a period of about 3 months or more, about 6 months or more, or about 12 months or more. In another example, a stable fentanyl formulation includes about 2% or less, about 1.5% or less, about 1% or less, about 0.75% or less, or about 0.5% or less of total impurities after storage of the formulation at about 40° C. for a period of 3 months or more, about 6 months or more, or about 12 months or more.

In one or more embodiments, a liquid parenteral fentanyl formulation includes a formulation that is stable for about 3 months or more, about 6 months or more, about 9 months or more, or about 12 months or more when stored at an accelerated temperature of about 40° C. In one or more embodiments, a ready-to-administer parenteral fentanyl formulation includes a formulation that is stable for about 6 months or more, about 12 months or more, about 18 months or more, or about 24 months or more when stored at long-term stability conditions.

The formulations of the present disclosure contain, as the active ingredient, fentanyl or any pharmaceutically acceptable salt thereof. In some embodiments, the formulations preferably contain fentanyl or any pharmaceutically acceptable salt thereof as the sole active ingredient characterized in that no other active ingredients are present in the formulation. In one example, the formulation contains only fentanyl citrate. The fentanyl or salt thereof, for instance fentanyl citrate, can be present in the formulation at a concentration of about 5 mcg/mL (micrograms/milliliter) or more, about 10 mcg/mL or more, about 15 mcg/mL or more, about 20 mcg/mL or more, or about 25 mcg/mL or more. In one or more embodiments, fentanyl (e.g., fentanyl citrate) can be present in the formulation at a concentration of about 0.5 mg/mL or less, 250 mcg/mL or less, 150 mcg/mL or less, about 100 mcg/mL or less, about 75 mcg/mL or less, about 50 mcg/mL or less, or about 40 mcg/mL or less.

In some embodiments, the ready-to-administer parenteral formulations contain a concentration of about 10 mcg/mL, about 15 mcg/mL, about 20 mcg/mL, or about 25 mcg/mL of fentanyl or a pharmaceutically acceptable salt thereof. In one or more embodiments, the ready-to-administer parenteral formulations contain about 0.5 mg, about 1 mg, about 2 mg, about 2.5 mg, about 5 mg, about 6.25 mg, about 10 mg, about 12.5 mg or about 15 mg of fentanyl or a pharmaceutically acceptable salt thereof per storage container (e.g., polymeric infusion bag).

The formulations can be supplied or stored in any suitable volume for parenteral administration. In one or more embodiments, the formulation volume (e.g., amount of liquid in a storage container) is about 25 mL or more, about 50 mL or more, about 75 mL or more, about 100 mL or more, about 150 mL or more, about 200 mL or more, about 250 mL or more, about 300 mL or more, or about 500 mL or more. For example, the formulation volume can be about 50 mL to about 500 mL, about 75 mL to about 300 mL, or about 100 mL to about 250 mL. In some embodiments, the formulation volume is about 50 mL, about 100 mL, about 150 mL, about 200 mL, or about 250 mL. Appropriate-sized containers for storing formulation volumes can be determined by one of ordinary skill in the art.

The formulations can be stored in or supplied in any suitable container. For example, the formulation can be in a container that includes, but is not limited to, infusion container, bag (IV bag), bottle (IV bottle), or vial. In one or more embodiments, container can be a polymeric infusion bag, for example, having an aluminum over pouch. The infusion container can be a flexible plastic container, optionally with ports and closure system for storing the fentanyl formulations. Infusion containers can include other conventional components, for example, connection ports, connector caps or connector disks. The container can be made of any suitable material, for instance, a polymeric or plastic material, or glass. Example materials for the containers and container components can include polyolefins, polysulfone, polycarbonate, polypropylene, polyethylene (LDPE or HDPE), ethylene/propylene copolymers, acrylic-imide copolymers, polyester (e.g. PET, PEN and the like), Teflon, Nylon, acetal (Delrin), polymethylpentene, PVDC, ethylvinylacetate, AN-copolymer or polyioprene. Preferably, the materials for the container and container components are suitable to withstand aseptic filling and not deform during terminal sterilization.

The container for holding and storing the fentanyl formulations can be supplied as a non-sterile container. After filing, the non-sterile container holding the fentanyl formulation is terminally sterilized to provide a stable parenteral product. In one or more embodiments, prior to filling the formulation in a container, the container is preferably sterile and has been subjected to a sterilization process prior to filing with the formulations of the invention, for example, under aseptic conditions. Containers are sealed as typical in the industry, for example, with the use of a lid, cap, closure and the like. Polymeric bags such as those manufactured by Technoflex and Polycine.

The formulations further include a pharmaceutically acceptable diluent. Examples of acceptable diluents include sodium chloride solutions (e.g., 0.9% NaCl solution) and Ringer's solution. In one or more embodiments, the diluent is free of a sugar, saccharide or sugar-alcohol compound. In a preferred embodiment, the diluent includes a sodium-containing compound, for example, an aqueous solution of a sodium-containing compound such as sodium chloride. The sodium-containing compound (e.g., NaCl) can be present in the formulation in a concentration range of about 1 mg/mL to about 50 mg/mL, about 2 mg/mL to about 25 mg/mL, about 3 mg/mL to about 20 mg/mL, about 5 mg/mL to about 15 mg/mL, or about 6 mg/mL, about 7 mg/mL, about 8 mg/mL, about 9 mg/mL, about 10 mg/mL, about 11 mg/mL, about 12 mg/mL, about 13 mg/mL or about 14 mg/mL.

To maintain the pH within the preferred range, in the ready-to-administer parenteral formulations as terminally sterilized or filled under aseptic conditions in the infusion container, the formulations can be buffered. For instance, a buffering agent or agents can be used to maintain the formulation at a pH of about 3 to about 4.5. The buffering agent can include one or more of acetate, glutamate, citrate, tartrate, benzoate, lactate, malate, gluconate, phosphate, glycine and combinations thereof. In one example, the buffering agent includes citric acid, sodium citrate or a combination thereof. Examples of sodium citrate include hydrates, sodium citrate dihydrate, trisodium citrate anhydrous, trisodium citrate dihydrate, and trisodium citrate pentahydrate. In other examples, the buffering agent includes a sodium-containing compound. When used with the fentanyl citrate, a citrate buffer system provides then counter ion to the fentanyl salt. In another example, the buffering agent includes acetic acid, sodium acetate or a combination thereof. Examples of sodium acetate include hydrates and sodium acetate anhydrous and acetic acid can be glacial acetic acid or anhydrous acetic acid.

Buffering agents can be present in the formulations at suitable concentrations, for example, in the arrange of about 0.1 to about 50 mM, about 1 to about 25 mM, or about 2 mM to about 12 mM for formulations containing about 5 mcg/mL to about 25 mcg/mL of fentanyl or any pharmaceutically acceptable salt thereof. In one or more embodiments, the formulation can include one or more buffer agents in the range of about 0.25 mg/mL to about 25 mg/mL, about 0.5 mg/mL to about 20 mg/mL, about 0.75 mg/mL to about 15 mg/mL, or about 1 mg/mL to about 10 mg/mL for formulations containing about 5 mcg/mL to about 25 mcg/mL of fentanyl or any pharmaceutically acceptable salt thereof. In one or more embodiments, the formulation can include one or more buffer agents (e.g., citric acid, acetic acid, sodium citrate, sodium acetate) at about 5 mg/mL or less, about 2.5 mg/mL or less, 1.5 mg/mL or less, 1 mg/mL or less, 0.75 mg/mL or less or 0.5 mg/mL or less for formulations containing about 5 mcg/mL to about 25 mcg/mL of fentanyl or any pharmaceutically acceptable salt thereof.

The formulations can further include a pH adjuster, for example, a single pH adjuster or one or more pH adjusters, for example, and acid or a base. The pH adjuster serves to aid in adjusting the pH of the aqueous formulation. The adjusted pH of the aqueous formulation can further aid in the solubilization and stability of fentanyl or any salt thereof in the liquid formulation. In one or more embodiments, the pH adjuster hydrochloric acid. In one or more embodiments, the pH adjuster is glacial acetic acid. In one or more embodiments, the pH adjuster is sodium hydroxide or sodium bicarbonate. The concentration of the pH adjuster can be any concentration suitable for adjusting the pH, such as, for example, 1 N acid or base. The formulations can have any suitable acidic pH. In an example, the formulation can have a pH of about 3, about 3.1, about 3.2, about 3.3, about 3.4, about 3.5, about 3.6 about 3.7, about 3.8, about 3.9, about 4, about 4.1, about 4.2, about 4.3, about 4.4, or about 4.5. In one or more embodiments, the formulation can have a pH in the range of about 3 to about 4.5, about 3.5 to about 4.5, about 3.5, to about 4.2, about 3.6 to about 4.2, about 3.7 to about 4.2, or about 3.8 to about 4.2. In another example, the pH of the formulation is the range from about 3 to about 3.8, about 3 to about 3.7, about 3 to about 3.6, about 3 to about 3.5, or about 3.2 to about 3.5.

Optional ingredients, such as tonicity agents, chelating agents, and preservatives, can be provided to the formulation at any stage in its preparation. In one or more embodiments, the formulations are free of preservatives, chelating agents (e.g., EDTA), or a combination thereof.

Procedures for filling the formulations of the present invention in infusion containers, such as a polymeric infusion bag, and their subsequent processing, for example, terminal sterilization and aseptic filling conditions, are known in the art. Processing techniques of the formulations filled in an infusion container preferably use a sterilization process to destroy or eliminate any microorganisms that may be present in the fentanyl formulations following preparation. For example, terminal heat sterilization can be used to destroy all viable microorganisms within the final, sealed infusion container of the fentanyl formulation. An autoclave is commonly used to accomplish terminal heat-sterilization of drug products in their final packaging.

In general, autoclave cycles in the pharmaceutical industry for terminal sterilization of the drug products are 121° C. for 10 to 20 minutes. The fentanyl formulations of the present invention can be autoclaved at a temperature ranging from 115 to 130° C. for a period of time ranging from about 5 to about 40 minutes with acceptable stability. Autoclaving is preferably carried out in the temperature range of about 119 to about 122° C. for a period of time ranging from about 10 to about 35 minutes, or about 20 to about 30 minutes. It was observed that the ready-to-administer formulations contained in an infusion container withstands the extreme conditions of autoclaving and remains stable, both in terms of fentanyl assay and impurity formation, physically and chemically, even upon being subjected to lengthy autoclaving (e.g., about 30 minutes or more) and subsequent long-term storage.

In some embodiments, terminal sterilization can be characterized by specifying a $F_0$ value. The $F_0$ value is measured in minutes and is the time required to provide the lethality equivalents to that provided at 121° C. for a stated time. That is, $F_0$ is the equivalent amount of time, in minutes at 121° C., which has been delivered to a product by a sterilization process, for instance, an autoclaving process. For example, the $F_0$ value of a saturated steam sterilization process is the lethality expressed in terms of equivalent time in minutes at a temperature of 121° C. delivered by the process to the product in its final container (e.g., an infusion container such as an IV bag).

Terminally sterilizing formulations above 30 minutes is considered to be a standard overkill cycle to ensure elimination of any microorganisms. The fentanyl formulations of the present disclosure exhibit long-term storage stability after terminal sterilization at standard overkill cycles, and at terminal sterilizations at reduced cycle temperatures and/or times, and thus provide advantageous benefits. For example, the fentanyl formulations can be subjected to standard processing techniques (e.g., autoclaving) without the need for adjustments to process variables such at exposure time or temperature. By processing the fentanyl formulations to standard terminal sterilization processes without needing to reduce exposure time or temperature, the formulations are ensured to be sterile. Terminal sterilizations at an $F_0$ time of 40 minutes or less, 35 minutes or less, 30 minutes or less, 25 minutes or less, 20 minutes or less or 15 minutes or less are suitable for providing the stable, ready-to-administer formulations of the present disclosure.

The formulations of the present invention can be filled in an infusion containing a head space. Storing injectable solutions in containers generally requires an inert head space (e.g., nitrogen or argon) to reduce the loss of stability. The fentanyl formulations can be filled into infusion containers by conventional methods without the need for filling under inert gas and purging of the head space to eliminate the presence of oxygen, for example, below 5 percent. As such, the fentanyl formulations can be utilized with a broad range of filling procedures without the need for modifying equipment or operating procedures to accommodate for inert gas filing conditions.

The formulations of the present disclosure are suitable for parenteral administration, for example, to a mammal to provide anesthesia. Preferably, the mammal is a human. The anesthesia can be general or regional. Example methods include administering to provide analgesic action of short duration during anesthetic periods, premedication, induction and maintenance, and postoperative periods such as in the recovery room, use as an opioid analgesic supplement in general or regional anesthesia, with a neuroleptic as an anesthetic premedication for the induction of anesthesia and as an adjunct in the maintenance of general and regional anesthesia, and for use as an anesthetic agent with oxygen in high risk patients, for example, patients having open heart surgery or complicated neurological or orthopedic procedures.

In order to demonstrate the practice of the present invention, the following examples have been prepared and tested. The examples should not, however, be viewed as limiting the scope of the invention. The claims will serve to define the invention.

EXAMPLES

Example 1

This example demonstrates the stability of exemplary formulations including fentanyl citrate, diluents and a chelating agent over a range of pH values. Separate samples containing the formulations of Table 1 below were prepared at the specified concentrations in the aqueous solutions and then the pH was adjusted with acid or base. The samples were filled into polymeric IV bags.

TABLE 1

| Formulation | pH | Bag Supplier |
|---|---|---|
| 0.01 mg/mL fentanyl 0.9% sodium chloride | Adjusted to 5.5 with HCl, NaOH | Technoflex |
| 0.01 mg/mL fentanyl 0.9% sodium chloride | Adjusted to 5.5 with HCl, NaOH | Polycine |
| 0.01 mg/mL fentanyl | Adjusted to 5.5 with HCl, | Polycine |

TABLE 1-continued

| Formulation | pH | Bag Supplier |
|---|---|---|
| 0.9% sodium chloride 0.2 mg/mL disodium EDTA 0.01 mg/mL fentanyl 5% dextrose | NaOH Adjusted to 5.5 with HCl, NaOH | Polycine |
| 0.01 mg/mL fentanyl 0.9% sodium chloride | Adjusted to 7 with NaOH | Polycine |
| 0.01 mg/mL fentanyl 0.9% sodium chloride | Adjusted to 4.5 with HCl | Polycine |

The formulations of Table 1 were analyzed for assay loss and pH change before and after terminal sterilization (TS) cycles (i.e. at different $F_0$ periods). The results are shown in Table 2 below.

TABLE 2

| Formulation and Container | Target $F_0$ (min) | pH before TS | pH after TS | Fentanyl Assay (%) before TS | Fentanyl Assay (%) after TS |
|---|---|---|---|---|---|
| 0.01 mg/mL fentanyl 0.9% sodium chloride Technoflex bag | 10 | 5.9 | 5.9 | 104.8 | 91 |
| 0.01 mg/mL fentanyl 0.9% sodium chloride Technoflex bag | 35 | 5.9 | 6.3 | 104.8 | 87 |
| 0.01 mg/mL fentanyl 0.9% sodium chloride Polycine bag | 10 | 5.7 | 5.6 | 105.5 | 91.5 |
| 0.01 mg/mL fentanyl 0.9% sodium chloride Polycine bag | 35 | 5.7 | 5.5 | 105.5 | 86.8 |
| 0.01 mg/mL fentanyl 0.9% sodium chloride Glass vial | No TS | 5.7 | N/A | 105 | N/A |
| 0.01 mg/mL fentanyl 0.9% sodium chloride 0.2 mg/mL EDTA Technoflex bag | 10 | 5.5 | 5.5 | 102.4 | 95.8 |
| 0.01 mg/mL fentanyl 0.9% sodium chloride 0.2 mg/mL EDTA Technoflex bag | 35 | 5.5 | 5.5 | 102.4 | 93.1 |
| 0.01 mg/mL fentanyl 0.9% sodium chloride 0.2 mg/mL EDTA Polycine bag | 10 | 5.5 | 5.5 | 102.2 | 95.8 |
| 0.01 mg/mL fentanyl 0.9% sodium chloride 0.2 mg/mL EDTA Polycine bag | 35 | 5.5 | 5.5 | 102.2 | 94.5 |
| 0.01 mg/mL fentanyl 0.9% sodium chloride 0.2 mg/mL EDTA Glass vial | No TS | 5.5 | N/A | 104.2 | N/A |
| 0.01 mg/mL fentanyl 5% dextrose Polycine bag | 35 | 4.5 | 4.6 | 101.5 | 96.3 |
| 0.01 mg/mL fentanyl 5% dextrose Glass vial | No TS | 4.5 | N/A | 102.3 | N/A |
| 0.01 mg/mL fentanyl 0.9% sodium chloride pH 6.4 Polycine bag 35 | 35 | 6.4 | 6.1 | 103.5 | 60.7 |
| 0.01 mg/mL fentanyl 0.9% sodium chloride pH 6.4 Glass vial | No TS | 6.4 | N/A | 103.8 | N/A |
| .01 mg/mL fentanyl 0.9% sodium chloride pH 4.5 Polycine bag | 35 | 4.7 | 4.7 | 102.9 | 99.4 |
| 0.01 mg/mL fentanyl 0.9% sodium chloride | No TS | 4.7 | N/A | 105.2 | N/A |

TABLE 2-continued

| Formulation and Container | Target $F_0$ (min) | pH before TS | pH after TS | Fentanyl Assay (%) before TS | Fentanyl Assay (%) after TS |
|---|---|---|---|---|---|
| pH 4.5 Glass vial | | | | | |
| 0.01 mg/mL fentanyl in WFI Technoflex bag | 35 | 5.8 | 5.4 | 99.4 | 81.3 |
| 0.01 mg/mL fentanyl in WFI Polycine bag | 35 | 5.7 | 5.5 | 99.9 | 79.6 |
| 0.01 mg/mL fentanyl in WFI Glass vial | No TS | 5.7 | N/A | 99.6 | N/A |

As can be seen from Table 2, formulations at or near a pH of 4.5 that include 0.9% sodium chloride aqueous solution exhibited a stable pH after a long terminal sterilization along with a fentanyl assay loss of less than 3.5 percent. The 0.9% sodium chloride aqueous solution exhibited significant fentanyl assay loss when the pH was 5.5 or above. The dextrose solution exhibited over a 5% fentanyl assay loss after terminal sterilization at a pH of 4.5. The water-for-injection (WFI) also exhibited significant fentanyl assay loss when terminally sterilized in an infusion bag. The inclusion of EDTA did not exhibit any significant benefit to fentanyl assay loss.

Example 2

This example demonstrates the stability of exemplary formulations including fentanyl citrate, a citrate buffer and a sodium-containing diluent. The pH of the formulations was adjusted to 4.5 with an acid and base. Separate samples containing the formulation of Table 3 below were prepared at the specified concentrations in an aqueous solution and filled into Polycine bags. The filled bags were terminally sterilized for 10 and 20 minutes.

TABLE 3

| Formulation | Target $F_0$ (min) | pH before TS | pH after TS | Fentanyl Assay (%) before TS | Fentanyl Assay (%) after TS |
|---|---|---|---|---|---|
| 0.01 mg/mL fentanyl 0.9% sodium chloride 6 mM citrate buffer at pH 4.5 | 10 | 4.4 | 4.5 | 99.1 | 97.8 |
| 0.01 mg/mL fentanyl 0.9% sodium chloride 6 mM citrate buffer at pH 4.5 | 20 | 4.4 | 4.5 | 99.1 | 96.1 |
| 0.01 mg/mL fentanyl 0.9% sodium chloride 6 mM citrate buffer at pH 4.5 0.2 mg/mL Na$_2$EDTA | 10 | 4.5 | 4.5 | 100 | 98.7 |
| 0.01 mg/mL fentanyl 0.9% sodium chloride 6 mM citrate buffer at pH 4.5 0.2 mg/mL Na$_2$EDTA | 20 | 4.5 | 4.6 | 100 | 97.3 |

The data from Table 3 exhibits that the citrate buffer is effective at maintaining pH after terminal sterilization along with minimal fentanyl concentration loss. Fentanyl concentration loss was about 1.3% for both formulations at a terminal sterilization of 10 minutes and thus the addition of EDTA did not appear to benefit the formulation. At 20 minutes, the addition of EDTA provided minimal benefit and reduced fentanyl loss from about 3% to about 2.7%.

Example 3

The effect of pH and citrate buffer concentration on the formulations is demonstrated in this example. A pH range of 3.5 to 5 was evaluated for fentanyl formulations with a sodium-containing diluent and citrate buffer. The pH of the formulations was adjusted with an acid and base. Separate samples containing the formulation of Table 4 below were prepared at the specified concentrations in an aqueous solution and filled into Polycine bags. The filled bags were terminally sterilized for 20 minutes.

TABLE 4

| Formulation | Target $F_0$ (min) | pH before TS | Fentanyl Assay (%) before TS | Fentanyl Assay (%) before TS |
|---|---|---|---|---|
| 0.01 mg/mL fentanyl 0.9% sodium chloride 6 mM citrate buffer at pH 3.5 | 20 | 3.5 | 100.1 | 101.2 |
| 0.01 mg/mL fentanyl 0.9% sodium chloride 6 mM citrate buffer at pH 4 | 20 | 4 | 101 | 99.6 |
| 0.01 mg/mL fentanyl 0.9% sodium chloride 6 mM citrate buffer at pH 4.5 | 20 | 4.5 | 101.7 | 97.5 |
| 0.01 mg/mL fentanyl 0.9% sodium chloride 6 mM citrate buffer at pH 5 | 20 | 5 | 102.5 | 90.1 |
| 0.01 mg/mL fentanyl 0.9% sodium chloride 2 mM citrate buffer 0.1 mg/mL Na$_2$EDTA | 20 | 4 | 100.6 | 99.4 |
| 0.01 mg/mL fentanyl 0.9% sodium chloride 6 mM citrate buffer 0.2 mg/mL Na$_2$EDTA | 20 | 4 | 101 | 100.1 |
| 0.01 mg/mL fentanyl 0.9% sodium chloride 10 mM citrate buffer 0.3 mg/mL Na$_2$EDTA | 20 | 4 | 101.7 | 100.6 |
| 0.01 mg/mL fentanyl 0.9% sodium chloride 6 mM citrate buffer | 20 | 4 | 101.6 | 99.9 |

As can be seen from Table 4, lowering the pH of the formulations decreases the loss of fentanyl concentration, with 4.5 and below being preferred. At a pH of 5, terminal sterilization of the formulations in a polymeric infusion bag results in significant fentanyl assay loss. At a pH of 3.5 and 4, the formulations exhibited no loss or minimal loss of fentanyl. Regarding change in citrate buffer concentration, there was no significant difference on fentanyl assay after terminal sterilization for any level of EDTA, including the formulation excluding EDTA. The results further exhibit no significant difference in fentanyl assay loss after terminal sterilization for any buffer concentrations ranging from 2 mM to 10 mM.

Example 4

Storage Stability of Fentanyl Formulation
Two fentanyl formulations were prepared and analyzed to investigate the suitability of the formulations in a polymer infusion bag. The formulations were prepared according to the following procedure.

80% of the final volume of water was added to a vessel followed by the addition of sodium chloride. The contents were mixed until the sodium chloride was dissolved. For the formulation containing EDTA, disodium EDTA dihydrate was added and dissolved. Sodium citrate dehydrate was added to the vessel and mixed until dissolved. Anhydrous citric acid was added to the solution and mixed until dissolved. If necessary, the pH of the solution was adjusted to 4, either by addition of an acid (e.g., hydrochloric acid) or a base (e.g., sodium hydroxide), before fentanyl citrate (as a concentrate in water) was added and mixed. Water was then added to bring to final desired volume. The pH of the final solution was checked and adjusted to 4 with an acid or base. The bulk solutions, 104 mL per bag, as referenced in Tables 5 and 6 below, were filled into Polycine, single port IV bags under ambient headspace and closed with a polypropylene twist-off stopper. The container closure system is provided in Table 7 below.

The filled bags were terminally sterilized in a Fedegari autoclave using an air overpressure cycle with a target $F_0$ of 20 or 35 minutes.

TABLE 5

| Ingredient | Concentration |
|---|---|
| Fentanyl citrate | 15.71 mcg/mL |
|  | (10 mcg/mL as fentanyl base) |
| Sodium chloride | 9 mg/mL |
| Sodium citrate dihydrate | 0.742 mg/mL |
| Citric acid anhydrous | 0.668 mg/mL |
| 1N hydrochloric acid solution | pH adjustment |
| 1N sodium hydroxide solution | pH adjustment |
| Water for Injection (WFI) | q.s. to 1 mL |

TABLE 6

| Ingredient | Concentration |
|---|---|
| Fentanyl citrate | 15.71 mcg/mL |
|  | (10 mcg/mL as fentanyl base) |
| Sodium chloride | 9 mg/mL |
| Sodium citrate dihydrate | 0.742 mg/mL |
| Citric acid anhydrous | 0.668 mg/mL |
| Disodium EDTA dihydrate | 0.2 mg/mL |
| 1N hydrochloric acid solution | pH adjustment |
| 1N sodium hydroxide solution | pH adjustment |
| Water for Injection (WFI) | q.s. to 1 mL |

TABLE 7

| Component | Description |
|---|---|
| IV bag and tube | 100 cc: Polycine APP114 multilayer polyolefin/styrene block copolymer, 200 μm |
|  | Tube: APP107, 1000 μm |
|  | 250 cc: Polycine APP114 multilayer polyolefin/styrene block copolymer, 200 μm |
|  | Tube: APP107, 1000 μm |
| Twist-off stopper | Polypropylene twist-off, TP823 |
| Overwrap | Film 140 MM Width × 265 MM, Climaprop II (12PET/9ALU/80PE) |
|  | Film 140 MM Width × 290 MM, Climaprop II (12PET/9ALU/80PE) |

The IV bags were tested for pH at intervals through six months of testing at long-term and accelerated storage conditions. Long-term storage conditions were at about 25° C. at about 60% relative humidity (RH) or 25±2° C., 60±5% RH and accelerated storage conditions were about 40° C. at about 75% relative humidity (RH) or 40±2° C., 75±5% RH. The results are shown in Table 8 below.

TABLE 8

| Formulation | Storage Conditions | Initial pH | 3-month Stability pH | 6-month Stability pH | 12-month Stability pH |
|---|---|---|---|---|---|
| Table 6, 100 mL bag, $F_0$20 | Long-term | 4 | 4 | 4.1 | 4 |
| Table 6, 100 mL bag, $F_0$20 | Accelerated | 4 | 4 | 4.1 | — |
| Table 6, 100 mL bag, $F_0$35 | Long-term | 4 | 4 | 4.1 | 4 |
| Table 6, 100 mL bag, $F_0$35 | Accelerated | 4 | 4 | 4.1 | — |
| Table 6, 250 mL bag, $F_0$35 | Long-term | 4 | 3.9 | 4 | — |
| Table 6, 250 mL bag, $F_0$35 | Accelerated | 4 | 4 | 4.1 | — |
| Table 5, 100 mL bag, $F_0$35 | Long-term | 4 | 3.9 | 4 | 4 |
| Table 5, 100 mL bag, $F_0$35 | Accelerated | 4 | 4 | 4.1 | — |

As can be seen in Table 8, after 3 months at long term and accelerated storage conditions, the non-EDTA formulations exhibited a pH of 3.9 and 4, respectively. At 6 months, the measured pH was 4 and 4.1 and, after 12 months, the measured pH was 4. Thus, there was no change in pH of the non-EDTA formulation after 6 months of long term and 6 months at accelerated storage in an IV bag. The presence of EDTA in the formulation did not show a benefit to maintaining pH as compared to the non-EDTA formulation.

The fentanyl concentration of the formulations in the IV bags was assayed at 3, 6 and 12 months as compared to the initial measured assay. The long-term and accelerated conditions are the same as specified for Table 8. The results are shown in Table 9 below.

TABLE 9

| Formulation | Storage Conditions | Initial Assay | 3-month Stability Assay | 6-month Stability Assay | 12-month Stability Assay |
|---|---|---|---|---|---|
| Table 6, 100 mL bag, F020 | Long-term | 98.4 | 98.6 (0.2%) | 98.6 (0.2%) | 98.6 (0.2%) |
| Table 6, 100 mL bag, F020 | Accelerated | 98.4 | 98.6 (0.2%) | 98.6 (0.2%) | — |
| Table 6, 100 mL bag, F035 | Long-term | 99.7 | 98.9 (−0.8%) | 99.2 (−0.5%) | 98 (−1.7%) |
| Table 6, 100 mL bag, F035 | Accelerated | 99.7 | 98.6 (−1.1%) | 98.9 (−0.8%) | — |
| Table 6, 250 mL bag, F035 | Long-term | 98.6 | 98.5 (−0.1%) | 99 (0.4%) | — |
| Table 6, 250 mL bag, F035 | Accelerated | 98.6 | 98.8 (0.2%) | 99.1 (0.5%) | — |
| Table 5, 100 mL bag, F035 | Long-term | 101.1 | 101 (−0.1%) | 101 (−0.1%) | 99.9 (−1.2%) |
| Table 5, 100 mL bag, F035 | Accelerated | 101.1 | 99.9 (−1.2%) | 101.2 (0.1%) | — |

As can be seen in Table 9, at long term storage conditions, the non-EDTA fentanyl concentration was respectively 101, 101 and 99.9 for 3, 6 and 12 months Thus, the concentration of fentanyl in the non-EDTA formulation did not change at storage conditions of long-term stability (25±2° C., 60±5% RH). At accelerated conditions, the fentanyl concentration of the non-EDTA formulation was respectively 99.9 and 101.2 for 3 and 6 months. Again, the concentration of fentanyl in the non-EDTA formulation did not change at storage conditions of accelerated stability (40±2° C., 75±5% RH). The presence of EDTA in the formulation did not show a notable benefit to maintaining fentanyl concentration as compared to the non-EDTA formulation.

The impurity concentration of the formulations in the IV bags was assayed at 3, 6 and 12 months as compared to the initial measured impurity concentration. The long-term and accelerated conditions are the same as specified for Table 8. The results are shown in Table 10 below.

TABLE 10

| Formulation | Storage Conditions | Initial Total Impurity | 3-month Total Impurity | 6-month Total Impurity | 12-month Total Impurity |
|---|---|---|---|---|---|
| Table 6, 100 mL bag, F020 | Long-term | <LOQ | <LOQ | <LOQ | <LOQ |
| Table 6, 100 mL bag, F020 | Accelerated | <LOQ | 0.29 | 0.36 | — |
| Table 6, 100 mL bag, F035 | Long-term | 0.53 | <LOQ | <LOQ | <LOQ |
| Table 6, 100 mL bag, F035 | Accelerated | 0.53 | 0.31 | 0.37 | — |
| Table 6, 250 mL bag, F035 | Long-term | <LOQ | <LOQ | <LOQ | — |
| Table 6, 250 mL bag, F035 | Accelerated | <LOQ | <LOQ | 0.22 | — |
| Table 5, 100 mL bag, F035 | Long-term | 0.38 | <LOQ | <LOQ | <LOQ |
| Table 5, 100 mL bag, F035 | Accelerated | 0.38 | 0.11 | 0.36 | — |

Table 10 shows that the formulations are stable up to 3 months or more, up to 6 months or more, and up to 12 months or more with no significant total impurity change. For example, at storage conditions of long-term stability both formulations exhibited no change in the total impurity concentration, which further indicates that there was no change in any individual impurity. At accelerated storage conditions both formulations exhibited essentially no change in total impurity concentration, which again indicates that there was no change in any individual impurity.

Osmolality of the formulations at both test conditions was also measured at 3, 6 and 12 months. The osmolality of both formulations did not change at 3, 6 or 12 months as compared to the initial osmolality measurement at time zero. Weight variation of the formulations at both test conditions was also measured at 3, 6 and 12 months. The weight of both formulations did not change at 3, 6 or 12 months as compared to the initial weight measurement at time zero.

Example 5

Stability of Fentanyl Formulation

A fentanyl formulation was prepared and analyzed to investigate the suitability of the formulations in a polymer infusion bag when including an acetate buffer. The formulation was prepared according to the following procedure.

80% of the final volume of water was added to a vessel followed by the addition of sodium chloride. The contents were mixed until the sodium chloride was dissolved. Sodium acetate anhydrous was added to the vessel and mixed until dissolved. Glacial acetic acid was added to the solution and mixed until dissolved. If necessary, the pH of the solution was adjusted to 4, either by addition of an acid (e.g., hydrochloric acid) or a base (e.g., sodium hydroxide), before fentanyl citrate (as a concentrate in water) was added and mixed. Water was then added to bring to final desired volume. The pH of the final solution was checked and adjusted to 4 with an acid or base. The bulk solutions, 104 mL per bag, as referenced in Table 11 below, were filled into Polycine, single port IV bags under ambient headspace and closed with a polypropylene twist-off stopper. The container closure system is provided in Table 12 below.

As a control, the bulk solution was also filled into a glass vial with a coated stopper and terminally sterilized the same as the filled bags as noted below. Bulk solution that did not undergo terminal sterilization was analyzed alongside the terminally sterilized samples for appearance, assay, pH and impurities.

The filled bags were terminally sterilized in a Fedegari autoclave at 121° C. using an air overpressure cycle with a target $F_0$ of 20 minutes.

TABLE 11

| Ingredient | Amount per mL |
|---|---|
| Fentanyl citrate | 0.01 mg as fentanyl base |
| Sodium chloride | 9 mg |
| Sodium acetate anhydrous | 0.11 mg |
| Glacial acetic acid | 0.28 mg |
| 1N hydrochloric acid solution | pH adjustment |
| 1N sodium hydroxide solution | pH adjustment |
| Water for Injection (WFI) | q.s. to 1 mL |

TABLE 12

| Component | Description |
|---|---|
| IV Bag and Tube | 100 cc: Polycine APP114 multilayer polyolefin/styrene block copolymer, 200 μm Tube: APP107, 1000 μm |
| Twist-off Stopper | Polypropylene twist-off, TP823 |
| Overwrap | Film 140 MM Width × 265 MM, Climaprop II (12PET/9ALU/80PE) |

The IV bag and glass vial were tested for appearance, pH, assay and impurities after terminal sterilization. The results are shown in Table 13 below.

TABLE 13

| Test | Control (no terminal sterilization) | Terminally Sterilized Glass Vial | Terminally Sterilized IV Bag |
|---|---|---|---|
| Appearance | Clear, colorless solution | Clear, colorless solution | Clear, colorless solution |
| pH | 4.0 | 4.0 | 4.0 |
| Assay (%) | 100.9 | 100.6 | 99.2 |
| Total Degradation Products (%) | <LOQ | 0.14 | 0.94* |

*Portion of impurity is believed to be a bag leachable and thus total degradation products is lower for formulation.

Table 13 shows that the appearance and pH of the terminally sterilized glass vial and IV bag was unchanged as compared to the non-terminally sterilized control bulk solution. There was minimal loss in fentanyl assay after terminal sterilization of the glass vial and IV bag. The terminally sterilized IV bag exhibited a fentanyl assay of greater than 99%, which was similar to the same formulation with a citrate buffer instead of the acetate buffer. The terminally sterilized IV bag also exhibited no significant change in total impurity with a total degradation product of less than 1 percent. The results of Example 5 indicate that the acetate buffer system is suitable for use in a ready-to-administer parenteral formulation that remains stable over time and requires terminal sterilization, whether in an IV bag (e.g., a polymeric IV bag) or a glass vial.

Many variations and modifications may be made to the above-described embodiments of the disclosure without departing substantially from the spirit and various principles of the disclosure. All such modifications and variations are intended to be included herein within the scope of this disclosure and protected by the following claims.

What is claimed is:

1. A ready-to-administer parenteral liquid formulation comprising:
   a. 5 mcg/mL to about 25 mcg/mL of fentanyl citrate;
   b. a sodium-containing diluent; and
   c. about 0.5 mg/mL to about 5 mg/mL of a buffer;
      wherein the ready-to-administer parenteral liquid formulation has a pH of about 3 to about 4.5 and has been terminally sterilized in a polymeric infusion container, wherein the ready-to-administer parenteral liquid formulation is stable for at least 6 months at about 40° C.

2. The ready-to-administer parenteral liquid formulation of claim 1, wherein the buffer comprises at least one of citric acid, sodium citrate, acetic acid, sodium acetate or a combination thereof.

3. The ready-to-administer parenteral liquid formulation of claim 1, wherein the formulation has a volume of from about 50 mL to about 500 mL and the polymeric infusion container is a bag terminally sterilized by autoclaving.

4. The ready-to-administer parenteral liquid formulation of claim 1, wherein the formulation is free of a sugar-alcohol.

5. The ready-to-administer parenteral liquid formulation of claim 1, wherein the sodium-containing diluent is aqueous sodium chloride solution and the pH is about 3.5 to about 4.5.

6. The ready-to-administer parenteral liquid formulation of claim 1, wherein the formulation contains about 1.0% or less of an individual impurity after storage for 6 months at about 40° C. or for 12 months at about 25° C.

7. The ready-to-administer parenteral liquid formulation of claim 1, wherein the formulation contains about 1.0% or less of total impurities after storage for 6 months at about 40° C. or for 12 months at about 25° C.

8. The ready-to-administer parenteral liquid formulation of claim 1, wherein the formulation retains about 98% or more of the initial concentration of fentanyl or a pharmaceutically acceptable salt thereof after storage for 6 months at about 40° C. or for 12 months at about 25° C.

9. A method of treating a patient in need of anesthesia by administering to the patient a ready-to-administer parenteral liquid formulation of claim 1.

* * * * *